United States Patent

Schaldach et al.

[11] Patent Number: 5,626,624
[45] Date of Patent: May 6, 1997

[54] ARRANGEMENT FOR CONTROLLING A PACEMAKER

[75] Inventors: Max Schaldach, Erlangen; Gustav Boheim, Bad Bergaabern, both of Germany

[73] Assignee: Biotronik Mess-und Therapiegeraete GmbH & Co. Ingenieurbuero Berlin, Berlin, Germany

[21] Appl. No.: 403,702

[22] PCT Filed: Sep. 16, 1993

[86] PCT No.: PCT/DE93/00890

§ 371 Date: Mar. 17, 1995

§ 102(e) Date: Mar. 17, 1995

[87] PCT Pub. No.: WO94/06513

PCT Pub. Date: Mar. 31, 1994

[30] Foreign Application Priority Data

Sep. 17, 1992 [DE] Germany ............ 42 31 601.4

[51] Int. Cl.$^6$ .................................................. A61N 1/368
[52] U.S. Cl. ..................... 607/24; 128/734; 128/713
[58] Field of Search ............................... 128/713, 734; 607/24

[56] References Cited

U.S. PATENT DOCUMENTS

| | | |
|---|---|---|
| 4,686,987 | 8/1987 | Salo et al. |
| 4,702,253 | 10/1987 | Nappholz et al. |
| 4,733,667 | 3/1988 | Olive et al. |
| 5,036,849 | 8/1991 | Hauck et al. ............ 607/24 |
| 5,058,583 | 10/1991 | Geddes et al. |
| 5,074,303 | 12/1991 | Hauck |
| 5,154,171 | 10/1992 | Chirife ................... 607/24 |

FOREIGN PATENT DOCUMENTS

| | | |
|---|---|---|
| 0140472 | 5/1985 | European Pat. Off. |
| 0327292 | 8/1989 | European Pat. Off. |
| 3629587 | 3/1987 | Germany |
| 3914680 | 11/1990 | Germany |
| 92/05836 | 4/1992 | WIPO |
| 92/11901 | 7/1992 | WIPO |

OTHER PUBLICATIONS

G. Boheim et al.: "Frequenzadaption eines künstlichen Hetzschrittmachers über einen Volumenregelkreis". In: Biomed. Technik, vol. 33, No. 5, 1988, pp. 100–105.

G. Boheim et al.: "Intrakardiale Impedanzmessung zur Regelung frequenzadaptiver Schrittmachersystems". In: Biomedizinische Technik, vol. 32, Sep. 1987, Berlin, Germany, pp. 41–42.

J.L. Wessale et al.: "Use of electrical impedance for continuous measurement of stroke volume of skeletal muscle–powered cardiac assist device". In:Medical & Biological Engineering & Computing, Mar. 91, pp. 207–211.

C. Barak et al.: "Simulation method for cardiac stroke volume estimation by intracardiac elecrical impedance measurement". In: Medical & Biological Engineering & Computing, Sep. 1992, pp. 473–480.

Primary Examiner—William E. Kamm
Assistant Examiner—Kennedy J. Schaetzle
Attorney, Agent, or Firm—Spencer & Frank

[57] ABSTRACT

An arrangement is provided for controlling a stimulation frequency of a pacemaker. The arrangement includes an atrial bipolar electrode system and a ventricular bipolar electrode system. A first electrode pair comprises an electrode from each of the atrial and ventricular bipolar electrode systems, with the electrodes of the first electrode pair being disposed intracardially in the atrium and ventricle, respectively. A pacemaker control unit generates stimulation pulses for stimulating the heart. A constant current source impresses a constant current to a second electrode pair, comprising at least one electrode from one of the atrial and ventricular bipolar electrode systems being disposed intracardially in one of the atrium and ventricle, for developing an electrical potential between the electrodes of the first electrode pair during predetermined cardiac phases. An impedance measuring unit measures impedance between the electrodes of the first electrode pair based upon the electrical potential and constant current and generates a control signal representing relative cardiac volume as a function of the measured impedance. The control signal is fed to the pacemaker control unit for influencing a stimulation frequency of the stimulation pulses.

16 Claims, 3 Drawing Sheets

ARRANGEMENT FOR CONTROLLING A PACEMAKER

This application is a 371 of PCT/DE93/00890, filed Sep. 16, 1993.

BACKGROUND OF THE INVENTION

The invention relates to an arrangement for controlling a pacemaker in which a control signal corresponding to cardiac volume is generated by an impedance measurement with the aid of electrodes disposed intracardially, which signal is used for influencing the stimulation frequency of the stimulation pulses of the pacemaker.

Different measuring values can be used to control the stimulation frequency of a pacemaker.

On the basis of new realizations, physiological parameters, such as temperature of the venous blood, breathing frequency or other intrathoracic function parameters of the patient, when extensively matched to one another, are preferably used to control the stimulation frequency. Likewise, it is possible to adapt the stimulation frequency of the pacemaker to certain stress situations of the patient using the detection of the stroke volume or cardiac volume.

An arrangement is known from DE-OS 36 29 587 with which the ventricular volume can be determined in connection with an impedance measurement. According to this document, an intracavitary impedance catheter is used. This impedance catheter comprises a tube that is to be inserted intraventicularly and has a plurality of pairs of surface electrodes disposed at a distance from one another. These electrodes are activated by a corresponding number of electrical signals having respectively different frequencies, and serve as a current source or voltage-measuring points. The instantaneous ventricular volume can be calculated from the measured voltage, the magnitude of the impressed current and a few patient-specific, geometrical values. The precision of the method can be increased with an increasing number of electrode pairs. The stroke volume results from the difference between the calculated minimum volume for the end systole and the maximum volume for the end diastole.

The proposed multipole impedance catheter is basically suited for determining the ventricular volume. However, for use in connection with permanently implanted pacemakers, it has the significant disadvantage that the necessary larger number of which are installed parallel to each other and are insulated from one another, is associated with a considerable structural expenditure, if a reliable connection of the corresponding electrodes is to be assured in the bending stresses of the impedance catheter necessitated by the permanent use. A further disadvantage is that the necessary multipole plug connection to the pacemaker leads to a considerable increase in volume. Moreover, in the proposed measuring method, it is not possible to use electrode arrangements that are already implanted for an impedance measurement, so the additional plug connections even further increase the volume of the pacemaker.

SUMMARY OF THE INVENTION

An object of the invention is to provide an arrangement for controlling a pacemaker of the generic type named at the outset, in which conventional electrode systems that have been used successfully in connection with dual-chamber pacemakers can be used instead of a special multipole sensor to obtain a signal that correlates with the cardiac volume, with simultaneous, sufficient measuring precision.

This and other objects are accomplished in accordance with the invention wherein there is provided an arrangement for controlling a stimulation frequency of a pacemaker, comprising: an atrial bipolar electrode system; a ventricular bipolar electrode system; a first electrode pair comprising an electrode from each of the atrial and ventricular bipolar electrode systems, with the electrodes of the first electrode pair being disposed intracardially in the atrium and ventricle, respectively; a pacemaker control means for generating stimulation pulses for stimulating the heart; a constant current source for impressing a constant current to a second electrode pair comprising at least one electrode from one of the atrial and ventricular bipolar electrode systems for developing an electrical potential between the electrodes of the first electrode pair during predetermined cardiac phases, the at least one electrode of the second electrode pair being dispose intracardially in one of the atrium and ventricle; means for measuring an impedance between the electrodes of the first electrode pair based upon said electrical potential and said constant current, and generating a control signal representing relative cardiac volume as a function of the measured impedance, the control signal being fed to the pacemaker control means for influencing a stimulation frequency of the stimulation pulses.

The invention incorporates the realization that it is sufficient for a precise control of the stimulation frequency of the pacemaker to replace the measurement of the absolute volume of the cardiac chamber with a relative volume measurement. This type of procedure is justified in that, for adaptation of the stimulation frequency, the exact curve shape of the volume signal need not be determined, but rather only the change in relative values during defined, predetermined cardiac phases. A functional relationship between the measured impedance and the actual volume, regardless of type but essentially unambiguous, is sufficient.

The positioning of the intracardial leads used according to the invention in an atrium and in a ventricle of the heart of a patient permits impedance measurement over a relatively large volume, and thus, in an advantageous manner, leads to an improvement in measuring precision for the relative cardiac volume, whose value, calculated from the impedance measuring value, is used for the adaptation of the stimulation frequency of the pacemaker. The inclusion of the cardiac valve system located between atrium and ventricle in the blood volume used to measure impedance only insignificantly influences the measuring precision of the method, because possible sources of errors are eliminated due to the determination of the relative ventricular volume.

According to a preferred embodiment of the invention, implanted atrial and ventricular bipolar electrode leads of known design are used, in addition to stimulating the patient's heart, in impedance measurement. This omits the installation of additional electrodes, which is associated with a significant relief for the affected patient.

The atrial and ventricular bipolar electrode leads, which are particularly configured to be annular (i.e., ring electrodes), are used outside of the stimulation and sensing times to feed in a current from a constant-current source into the measuring volume. An electrical field builds up between the ring electrodes due to the impressed current. The potential gradient of the field can be tapped via the tip electrodes of the atrial and ventricular bipolar electrode leads as a measuring voltage that is proportional to the ventricular volume. The tip electrodes of the two bipolar electrode leads form a first electrode pair, and the ring electrodes form a second electrode pair.

The association of the individual electrodes of the atrial and ventricular leads, respectively, is effected by suitable switching means and their control elements, which are made available to the respectively active signal sources and signal sink as a function of the patient-dependent timing signal of the pacemaker via its central control and signal-processing unit.

According to a favorable refinement of the invention, the switching means are configured as bipolar change-over switches. They are associated in electrode pairs with the leads provided in the atrium and ventricle, respectively. Because of this, it is possible in a simple manner to effect the necessary association of the measured signals and stimulating pulses or control pulses between the intracardial electrodes and the central control and signal-processing unit, and to produce an impedance-measuring unit having the constant current source and a voltmeter. The change-over switches are always only operated when neither a stimulation pulse nor a sensing signal is present on the connecting lines between the intracardial electrodes and the central control and signal-processing unit of the pacemaker. For this task, commercially-available NOR elements are used with particular advantage as control elements of the switching means.

According to another advantageous refinement of the invention, one of the bipolar electrode leads positioned in the atrium or ventricle is replaced by a unipolar lead. To assure interference-free measuring and stimulation tasks of the pacemaker, the missing electrode is replaced by the housing of the pacemaker. In analogous fashion, other combinations of unipolar and/or bipolar sensors can serve in current feed-in, voltage measurement and stimulation.

BRIEF DESCRIPTION OF THE DRAWINGS

Advantageous refinements of the invention will be appreciated from the following detailed description taken in conjunction with the accompanying drawings.

DETAILED DESCRIPTION OF THE PREFERRED EMBODIMENT

Figure 1:
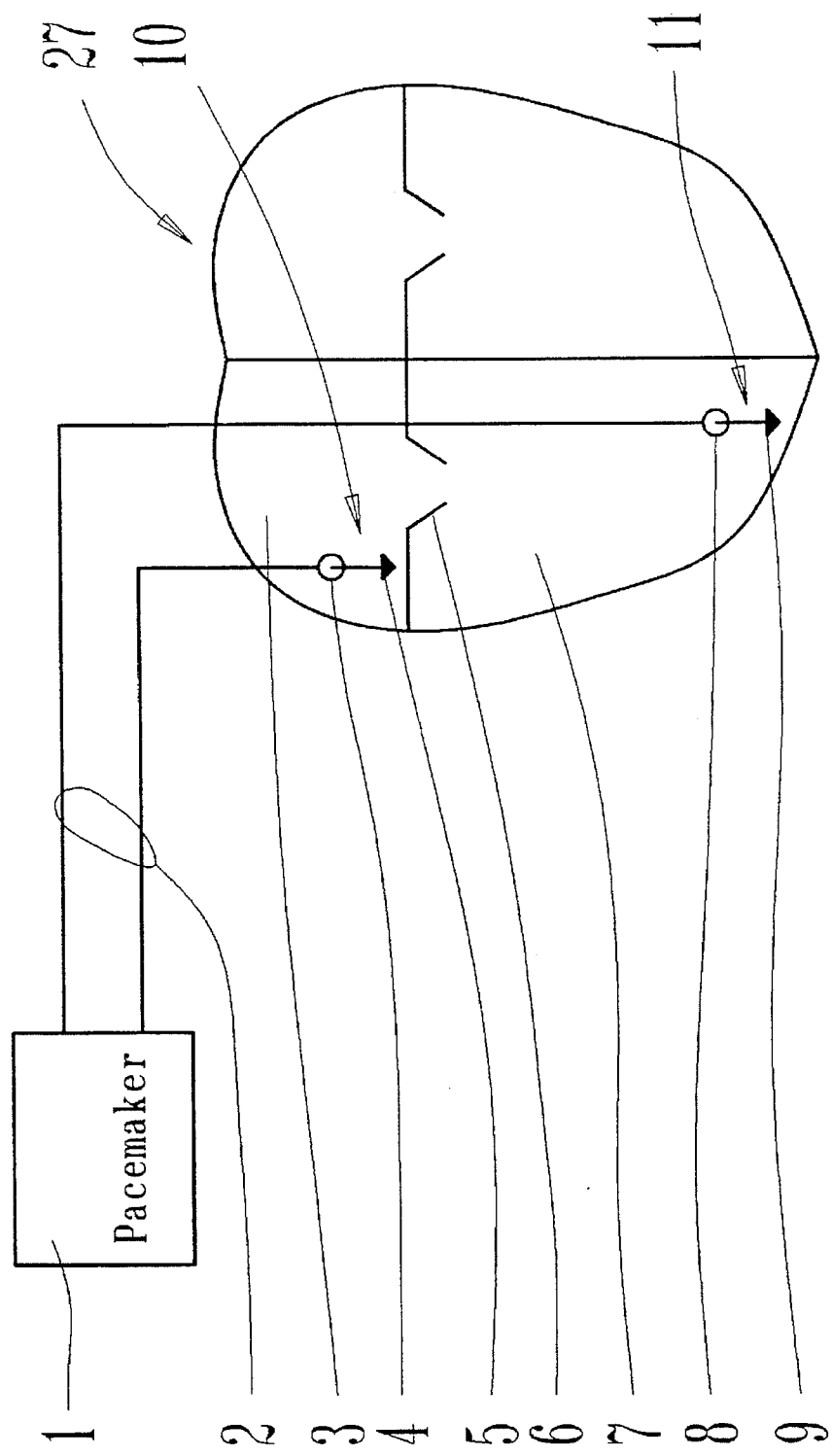
FIG. 1 shows an arrangement of the intracardial sensors according to a preferred embodiment of the invention in a schematized representation.

The schematized representation according to FIG. 1 shows the position of two electrode leads sensors 10, 11 inside the heart 27 for obtaining a signal correlating with the cardiac volume. The electrode leads 10, 11 are configured to be bipolar and respectively include a tip electrode 5, 9 and a ring electrode 4, 8. The leads 10, 11, which are connected to the pacemaker 1 by way of lines 2, are located in the atrium 3 and in the ventricle 7 of the heart 27. The atrial and ventricular tip electrodes 5, 9 and the atrial and ventricular ring electrodes 4, 8 of the individual sensors respectively form a first and a second electrode pair. The first electrode pair serves to detect the voltage that arises because a current is fed in by means of the second electrode pair, and the resulting potential difference via the blood resistance between the tip electrodes 5, 9. The instantaneous ventricular volume can be determined from the impedance determined from the measured voltage and the impressed current, and a few geometrical, heart-specific values so that the necessary adaptation of the stimulation frequency can be performed as a function of these.

Among other things, the relatively large spatial distance between the atrial and ventricular electrode leads 10, 11 is of particular advantage for the measuring precision of the method. In addition to voltage detection, the tip electrodes are also used to stimulate the heart's function (stimulating phase) and to detect the heart's reaction (sensing phase). Signal processing and generation of pulses for stimulation is effected by suitable devices of the pacemaker 1.

Figure 2:
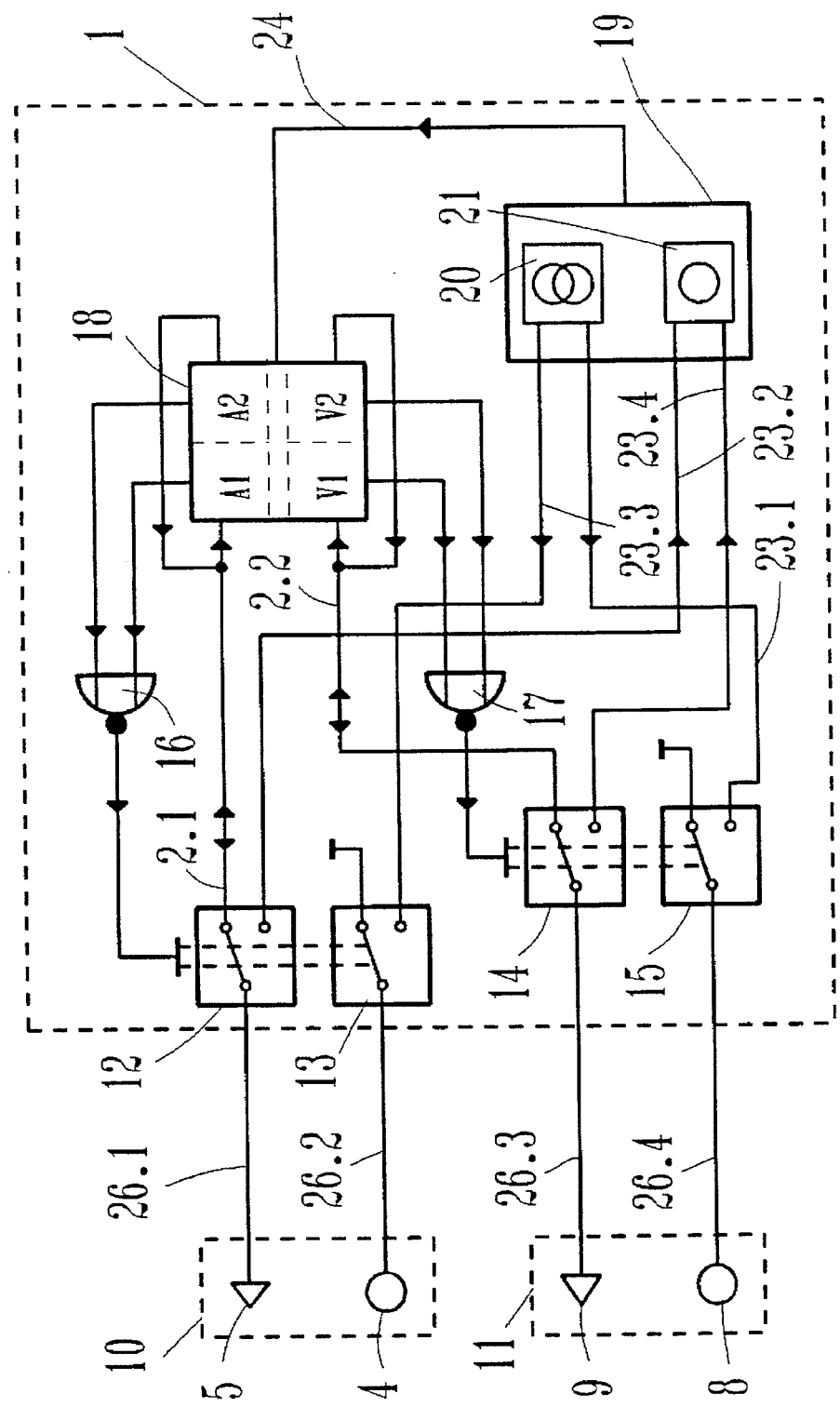
FIG. 2 is a block diagram of a preferred embodiment of an apparatus for performing the method.

The design of a preferred apparatus disposed in the pacemaker 1 and used for measuring impedance according to the invention is shown in block diagram form in FIG. 2. The apparatus includes a central control and signal-processing unit 18, which has four modules A1, A2, V1 and V2. Here, the control signals (sensing) for the separate reaction of the atrium 3 or the ventricle 7 are generated, as are the stimulation pulses as a function of the impedance to be measured. For this purpose, the modules A1, A2, V1 and V2 are connected by way of the lines 2.1 and 2.2 to controllable switching means 12 and 14, which in turn have a connection to the intracardial peak electrodes 5 and 9 of the bipolar electrode leads 10 and 11 via the lines 26.1 and 26.3. Furthermore, the apparatus includes an impedance-measuring unit 19, which is essentially subdivided into a constant-current source 20 and a voltmeter 21. The constant-current source 20 is connected by way of the lines 23.1 and 23.3, the controllable switching means 13 and 15 and the lines 26.2 and 26.4 to the ring electrodes 4 and 8 of the bipolar electrode leads 10, 11 for the purpose of impressing a constant current into the cardiac volume. The impedance measurement necessary for determining the cardiac volume is realized via the detection of the potential difference caused by the impressed constant current. For this purpose, the voltmeter 21 of the impedance-measuring unit 19 can likewise be connected to the intracardial tip electrodes 5, 9 by way of the lines 23.2 and 23.4, the controllable switching means 12 and 14 and the lines 26.1 and 26.3.

In order to be able to perform the check and control of the heart's function, and simultaneously the impedance measurement, for purposeful adaptation of the stimulation frequency by means of the pacemaker 1, the switching means 12, 13, 14, 15 are configured to be controllable as a function of the operating state of the central control and signal-processing unit 18. The switching means configured as two-pole change-over switches are associated in pairs with the intracardial sensors, and are controlled in pairs by the NOR functional blocks 16 and 17. The state illustrated in FIG. 2 determines the time range within which the central control and signal-processing unit 18 receives the sensing signals from the atrium or ventricle, or transmits stimulation pulses to these sections of the heart. The impedance-measuring unit 19 is separated from the atrial or ventricular sensor 10, 11 by the switching means 12, 13 and 14, 15. Outside of this time range, the NOR gates 16, 17 are switched due to the missing signal level at the modules A1, A2, V1, V2, and thus change the switching state of the switching means 12, 13, 14 and 15 to the effect that the connection of the sensors to the central control and signal-evaluating unit 18 is interrupted, and the constant-current source 20 is connected to the ring electrodes 4 and 8 of the leads 10 and 11 by way of the switching means 13 and 15, and the voltmeter 21 is connected to the tip electrodes 5 and 9 of the respective lead in the atrium 3 and the ventricle 7 by way of the switching means 12 and 14. For the purpose of controlling the stimulation frequency, the impedance values measured in the switching state of the switching means 12 through 15 are fed as a signal correlating with the momentary cardiac volume to the central control and signal-processing unit 18 by way of the line 24.

Figure 3:
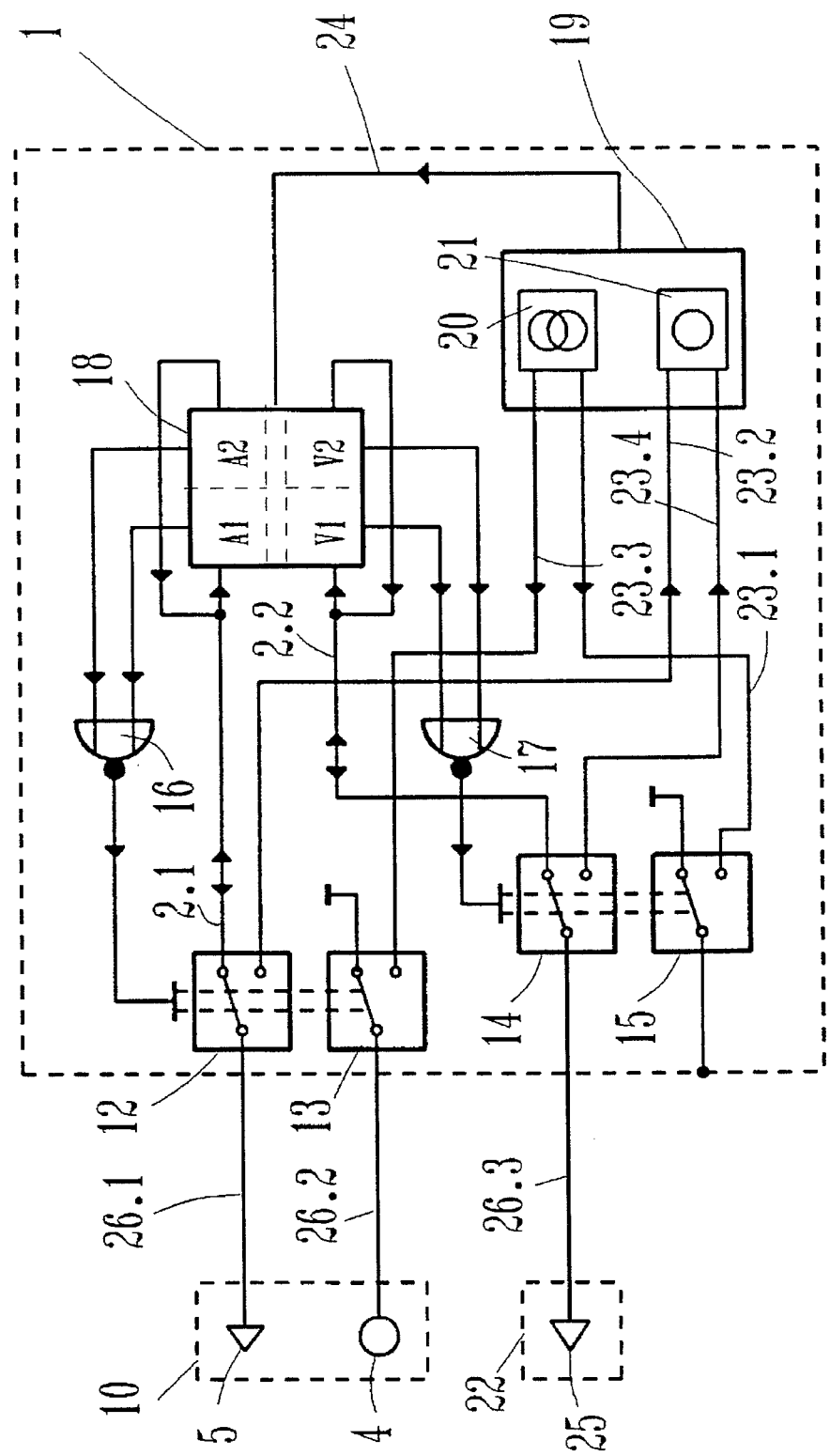
FIG. 3 is a block diagram of showing a favorable refinement of the apparatus shown in FIG. 2.

A refinement of the apparatus for measuring impedance is illustrated in the block diagram of FIG. 3. In this instance, the bipolar ventricular lead 11 is replaced by a unipolar lead 22 having the tip electrode 25. The missing fourth electrode is replaced by the potential of the housing of the pacemaker 1, so that the current from the constant-current source 20 can be fed in by way of the pacemaker housing and the ring electrode 4 of the atrial lead 10.

The invention is not limited in its configuration to the preferred embodiment disclosed above. Rather, a number of variations are conceivable which make use of the illustrated solution, even in embodiments that are of fundamentally different types.

We claim:

1. An arrangement for controlling a stimulation frequency of a pacemaker, comprising:

an atrial bipolar electrode system;

a ventricular bipolar electrode system;

a first electrode pair comprising an electrode from each of the atrial and ventricular bipolar electrode systems, with the electrodes of the first electrode pair being disposed intracardially in the atrium and ventricle, respectively;

a pacemaker control means for generating stimulation pulses for stimulating the heart;

a constant current source for impressing a constant current to a second electrode pair, comprising at least one electrode from one of the atrial and ventricular bipolar electrode systems disposed intracardially in one of the atrium and ventricle, for developing an electrical potential between the electrodes of the first electrode pair during predetermined cardiac phases; and means for measuring an impedance between the electrodes of the first electrode pair based upon said electrical potential and said constant current, and generating a control signal representing relative cardiac volume as a function of the measured impedance, the control signal being fed to the pacemaker control means for influencing a stimulation frequency of the stimulation pulses.

2. The arrangement according to claim 1, wherein the second electrode pair comprises an electrode from each of the atrial and ventricular bipolar electrode systems, and the electrodes of the second electrode pair are disposed intracardially in the atrium and ventricle, respectively.

3. The arrangement according to claim 1, wherein the pacemaker has a housing which comprises the other of the electrodes of the second electrode pair.

4. The arrangement according to claim 3, wherein the at least one electrode of the second electrode pair comprises a ring electrode and the constant-current source is connectable to the ring electrode of the second electrode pair and to the housing of the pacemaker.

5. The arrangement according to claim 1, wherein one of the electrodes of the atrial bipolar electrode system and of the ventricular bipolar electrode system is a ring electrode and the ring electrodes are disposed intracardially in the atrium and ventricle, respectively.

6. The arrangement according to claim 5, wherein the constant-current source is connected to the ring electrodes.

7. The arrangement according to claim 1, wherein one of the electrodes of the atrial bipolar electrode system and of the ventricular bipolar electrode system is a tip electrode, and the tip electrodes are disposed intracardially in the atrium and ventricle, respectively.

8. The arrangement according to claim 7, wherein the impedance measuring means includes a voltmeter which is connectable to the tip electrodes.

9. The arrangement according to claim 1, wherein at least one of the intracardial electrodes of the atrial bipolar electrode system comprises one of a sensing and stimulation electrode for the pacemaker.

10. The arrangement according to claim 1, wherein at least one of the intracardial electrodes of the ventricular bipolar electrode system comprises one of a sensing and stimulation electrode for the pacemaker.

11. The arrangement according to claim 1, wherein:

the pacemaker control means comprises a central control and signal-processing unit connected to at least one of the intracardial electrodes in at least one of the atrium and the ventricle for emitting stimulation pulse and for processing sensing pulses generated in the atrium and in the ventricle of the heart;

the arrangement further comprising:

a plurality of switching means each being connected, on the one hand, between a respective one of the bipolar electrode systems and the central control and signal-processing unit and, and on the other hand, between a respective one of the bipolar electrode systems and the impedance measuring means; and control elements each being connected to a respective one of the switching means and being activatable by the central control and signal-processing unit.

12. The arrangement according to claim 11, wherein the plurality of switching means comprise a plurality of two-pole change-over switches each being connected with a respective one of the electrodes of the atrial and ventricular bipolar electrode systems.

13. The arrangement according to claim 12, wherein the switches connected to the electrodes of the atrial bipolar electrode system are arranged to be switched together.

14. The arrangement according to claim 12, wherein the switches connected to the electrodes of the ventricular bipolar electrode system are arranged to be switched together.

15. The arrangement according to claim 11, wherein the control elements each comprise a NOR gate.

16. The arrangement according to claim 11, wherein the impedance-measuring means includes a voltmeter and the constant current source.

* * * * *